(12) United States Patent
Stewart et al.

(10) Patent No.: US 10,155,115 B2
(45) Date of Patent: *Dec. 18, 2018

(54) CARDIAC DEFIBRILLATION WITH VAGUS NERVE STIMULATION

(71) Applicant: The Research Foundation for The State University of New York, Albany, NY (US)

(72) Inventors: Mark Stewart, East Hanover, NJ (US); Isaac Naggar, Brooklyn, NY (US); Jason Lazar, Roslyn Heights, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,797

(22) Filed: Jun. 30, 2017

(65) Prior Publication Data

US 2017/0361102 A1 Dec. 21, 2017

Related U.S. Application Data

(63) Continuation of application No. 14/401,658, filed as application No. PCT/US2013/041613 on May 17, 2013, now Pat. No. 9,724,516.

(Continued)

(51) Int. Cl.
  *A61N 1/00* (2006.01)
  *A61N 1/36* (2006.01)
(52) U.S. Cl.
  CPC ..... *A61N 1/36139* (2013.01); *A61N 1/36053* (2013.01); *A61N 1/36114* (2013.01); *A61N 1/36171* (2013.01)

(58) Field of Classification Search
  USPC .......................................................... 607/62
  See application file for complete search history.

(56) References Cited

U.S. PATENT DOCUMENTS

| 2003/0158494 A1* | 8/2003 | Dahl ................... A61B 5/1076 600/526 |
| 2006/0271115 A1* | 11/2006 | Ben-Ezra ............. A61N 1/0556 607/5 |

(Continued)

FOREIGN PATENT DOCUMENTS

WO 2010/106823 A1 9/2010

OTHER PUBLICATIONS

Laun B. et al., Vliyanie Parasimpaticheskoi Nervnoi Sistemy Na Stabilnost Elektricheskoi Aktivnosti Zheludochkov Serdtsa. Materialy 2-go Sovetskogo-Americanskogo Simpoziuma (1979), (materialy i metody) [online]. Retrieved from the Internet: URL:http://lechebnik.info/440/17.htm.

(Continued)

*Primary Examiner* — Nicole F Johnson
*Assistant Examiner* — Nicole F. Lavert
(74) *Attorney, Agent, or Firm* — Scully, Scott, Murphy & Presser, P.C.

(57) ABSTRACT

A method and system for treating cardiac arrhythmias which includes inserting one or more electrodes into a patient's neck, and connecting the electrodes to the vagus nerve in the patient's neck. A cardiac monitoring device detects a cardiac arrhythmia. A controller connected to an electrical power source provides electrical power to the electrodes to apply electrical stimulation to the vagus nerve when a cardiac arrhythmia is detected.

28 Claims, 14 Drawing Sheets

Related U.S. Application Data

(60) Provisional application No. 61/648,436, filed on May 17, 2012.

(56) References Cited

U.S. PATENT DOCUMENTS

2010/0217343 A1  8/2010  Hamdan
2015/0134030 A1  5/2015  Stewart et al.

OTHER PUBLICATIONS

International Search Report dated Sep. 19, 2013 received in International Application No. PCT/US2013/041613.
Final US Office Action dated Nov. 4, 2016 received in U.S. Appl. No. 14/401,658.
US Office Action dated Apr. 4, 2016 received in U.S. Appl. No. 14/401,658.
US Office Action dated Oct. 9, 2015 received in U.S. Appl. No. 14/401,658.

\* cited by examiner

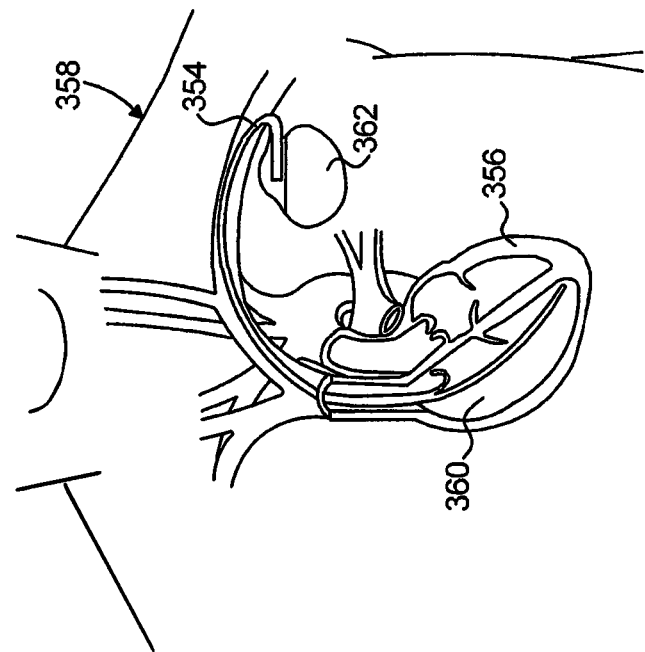
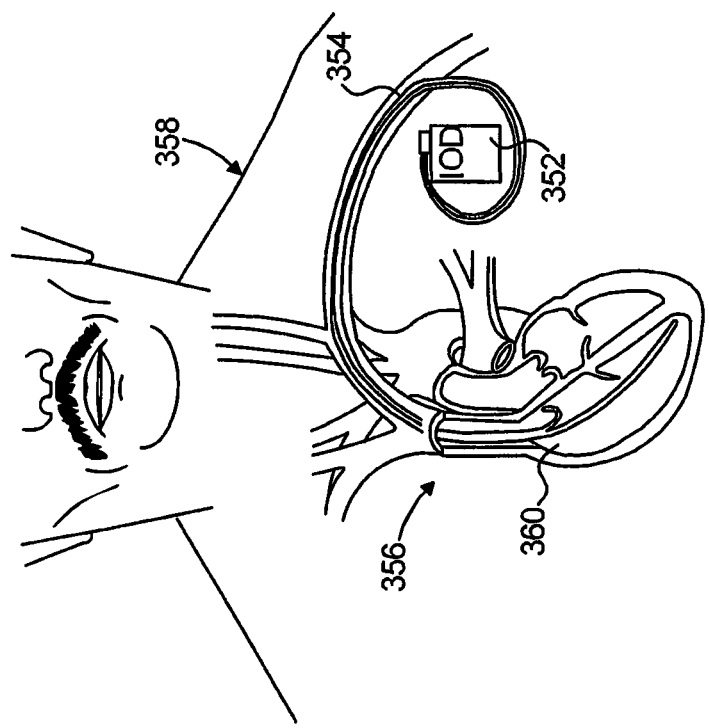
*Fig. 10A*
*Prior Art*
*Fig. 10B*
*Prior Art*

CARDIAC DEFIBRILLATION WITH VAGUS NERVE STIMULATION

CROSS-REFERENCE TO RELATED APPLICATIONS

The present application is a continuation of co-pending application having U.S. Ser. No. 14/401,658, filed on Nov. 17, 2014, which is a 371 of International application having Serial No. PCT/US2013/041613, filed on May 17, 2013, which claims the benefit of priority from U.S. Provisional Application No. 61/648,436, filed on May 17, 2012, the entire contents of all of which are incorporated herein by reference.

BACKGROUND OF THE INVENTION

1. Field of the Invention

The present invention generally relates to a method and system for vagus nerve stimulation for cardiac defibrillation, and more particularly, the present invention relates to a method and system for vagus nerve stimulation for cardiac defibrillation during ventricular fibrillation.

2. Description of Related Art

Preventative and protective treatment against cardiac arrhythmias including atrial fibrillation and ventricular fibrillation include vagus nerve stimulation (VNS). In one study, anesthetized dogs underwent coronary occlusion while undergoing medium and high intensity vagus nerve stimulation. The results were that hearts took longer to enter ventricular fibrillation (VF) during vagus nerve stimulation compared to controls. In another study vagus nerve stimulation (20 Hz trains) in anesthetized dogs lowered the threshold for intensity of shocks necessary for defibrillation.

Cardiac defibrillation with vagus nerve stimulation may include vagus nerve electrical stimulation providing protection against induced heart fibrillation/arrhythmia, and to lower the intensity of external electric shocks needed to defibrillate a fibrillating heart. However, defibrillator devices may require insertion of electrodes into the heart and ambulatory electrical defibrillator devices which require the insertion of electrodes into the heart are invasive, that is they invade the heart itself.

Existing implantable defibrillator devices that are placed via catheter to reach the ventricular lining in one or more locations have elements that cross one or more valves of the heart. Existing implantable defibrillators placed via access through a blood vessel, have an element of the device crossing the vessel wall. Thus, these devices have a risk of bleeding associated with the implant, and also a risk of causing valve damage.

Further, current use of vagus nerve stimulation is for activation of afferent nerve fibers (i.e., fibers intended to carry signals into brain). Afferent fibers are selected by the stimulus parameters because these fibers have a lower threshold for activation. Higher intensity stimuli required for activation of efferent vagal fibers (i.e., coming from brain to heart or other organs) will activate all vagal fibers (i.e., the high threshold efferent fibers cannot be selectively activated by adjusting stimulus parameters).

For illustrative purposes, referring to FIGS. 10A and 10B, a prior art implantable cardioverter-defibrillator (ICD) 352 (controller unit), 354 (wires), 360 (electrode) is shown in FIG. 10A, and a prior art pacemaker 362 (controller unit), 354 (wires), 360 (electrode) is shown in FIG. 10B. FIG. 10A shows the location and general size of the ICD 352 in the upper chest of a patient 358. Wires 354 with electrodes 360 on the ends are inserted into the heart 356 through a vein in the upper chest. FIG. 10B shows the location and general size of the pacemaker 362 in the upper chest of the patient 358. The wires 354 with electrodes 360 on the ends are inserted into the heart 356 through a vein in the upper chest of the patient 358.

Defibrillators are most commonly implanted through small incisions in the skin, near the collarbone. The patient is given a mild sedative, but is kept awake; a local anesthetic may be used. An electrophysiologist, a physician who specializes in heart rhythm problems, typically performs the procedure.

Using a fluoroscopy machine, which creates moving X-rays to visualize the chest's interior of a patient, an electrophysiologist guides the defibrillator leads through the incisions, into a large blood vessel, until they reach the heart. In the heart, the tip of each lead is attached to the heart muscle. Next, the leads are connected to the device's pulse generator, which is then placed in a pocket, just beneath the skin in the upper chest.

With the defibrillator in place, the electrophysiologist will perform a series of tests to ensure that device is working properly. An artificially fast heart rhythm might be programmed, e.g., fibrillation of the heart, to ensure that the leads are properly monitoring heart beats, and the pulse generator is sending the appropriate signals to stop the abnormal heart beat, e.g., defibrillation. Afterward, the device is programmed to meet the patient's needs. In this example, using existing ICD and defibrillation technology (e.g., implementing a shock to the heart), the device, the ICD, configuration includes electrically shocking the heart to causing fibrillation of heart for a period of time to configure the device for defibrillation. Thus, one disadvantage of this system for treatment is that the configuration technique of existing ICD devices is very stressful and dangerous for the patient by causing fibrillation during configuration.

When ventricular arrhythmias occur, the heart may not be able to pump blood well, and a patient can pass out within seconds and die within minutes if not treated. To prevent death, the arrhythmia must be treated immediately with an electric shock to the heart. This treatment is called defibrillation. An ICD has wires with electrodes on the ends that connect to a patient's heart chambers. The ICD can monitor a person's heart rhythm. If the device detects an irregular rhythm (e.g. ventricular tachycardia) in a person's ventricles, it will use low-energy electrical pulses to pace the heart in an attempt to restore a normal rhythm. If the low-energy pulses don't restore the person's normal heart rhythm, the ICD will switch to high-energy pulses for defibrillation. The device also will switch to high-energy pulses if the ventricles start to quiver (i.e., fibrillation) rather than contract strongly. The high-energy pulses last only a fraction of a second, but they can be painful, and therefore undesirable. In some instances, the pain from high-energy pulses can be severe, especially in cases of an administered defibrillation shock, such pain from repeated shocks can result in post traumatic stress disorder.

Doctors may also treat arrhythmias with another device called a pacemaker. An ICD is similar to a pacemaker, however, pacemakers give off only low-energy electrical pulses. They're often used to treat less dangerous heart rhythms, such as those that occur in the upper chambers of the heart. Some ICDs can act as both pacemakers and defibrillators.

SUMMARY OF THE INVENTION

It would be desirable to provide a treatment for cardiac arrhythmias including ventricular fibrillation to be used during fibrillation to defibrillate the heart, and which can be used exclusively, that is, without currently used electric shock treatment to a person's body delivering a therapeutic dose of electrical energy to the affected heart with a defibrillator device.

In an embodiment of the present invention, a method for treatment of cardiac arrhythmias including, atrial fibrillation, ventricular fibrillation, and ventricular tachycardia, includes vagus nerve stimulation, and during the arrhythmias, high frequency vagus nerve stimulation can be used on its own for defibrillation, without the need for a separate or additional defibrillator device.

In an aspect of the invention, a method for treating cardiac arrhythmias includes: inserting one or more electrodes into a patient's neck; connecting the electrodes to a vagus nerve in the patient's neck; detecting a cardiac arrhythmia; and initiating electrical power to the electrodes using a controller connected to an electrical power source to apply electrical stimulation to the vagus nerve when a cardiac arrhythmia is detected during a cardiac arrhythmia.

In another aspect of the invention, a system for treating cardiac arrhythmias includes one or more electrodes having a distal end insertable into a patient's neck and connectable at a distal end to a vagus nerve. A controller is connected to a proximal end of the electrodes. The controller is connected to an electrical power source for providing electricity to the electrodes for electrically stimulating the vagus nerve, wherein the electrical stimulation to the vagus nerve is applied during a cardiac arrhythmia. A cardiac monitoring device being configured to sense the heart's electrical activity.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 10A is a front view of the patient's heart using a prior art implantable cardioverter-defibrillator (LCD);

FIG. 10B is a front view of the patient's heart as shown in FIG. 10A using a prior art pacemaker;

DETAILED DESCRIPTION OF THE INVENTION

Figure 1:
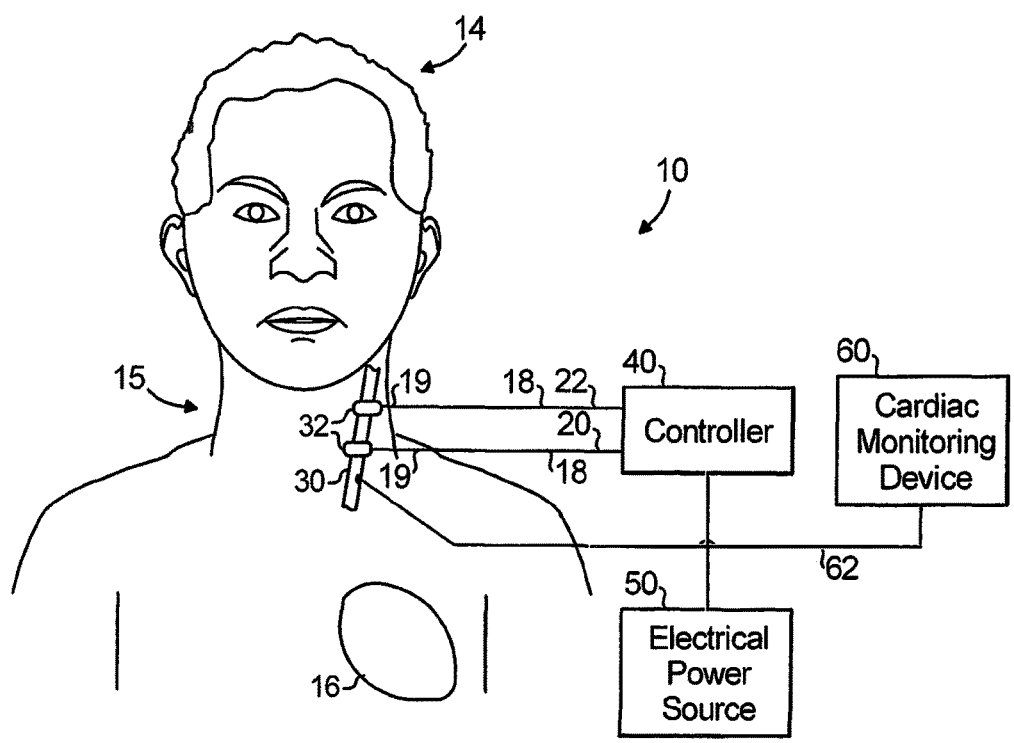
FIG. 1 is a schematic block diagram of a system according to an embodiment of the invention for treating cardiac arrhythmias.

Referring to FIG. 1, a system 10 for treating cardiac arrhythmias of a patient 14 includes electrodes 18 having a distal end 19 inserted into the patient's 14 neck 15. The electrodes 18 are connected at their distal end 19 to the vagus nerve 30, using connection elements 32. A controller 40 is connected to a proximal end 20 of the electrodes 18, wherein the controller 40 is connected to an electrical power source 50 for providing electricity to the electrodes 18 for electrically stimulating the vagus nerve 30. The electrical stimulation to the vagus nerve 30 is applied during a cardiac arrhythmia of the heart 16, thereby reversing the arrhythmia. The heart 16 is monitored by a cardiac monitoring device 60 for determining when cardiac arrhythmias occur. The cardiac monitoring device 60 monitors the heart using a connection 62 to the vagus nerve 30 and/or connection to the patient's chest wall in the vicinity of the controller implant. The cardiac arrhythmia or cardiac event may include ventricular fibrillation. The method and system described herein may be used to convert ventricular fibrillation to a normal cardiac rhythm.

Figure 2:
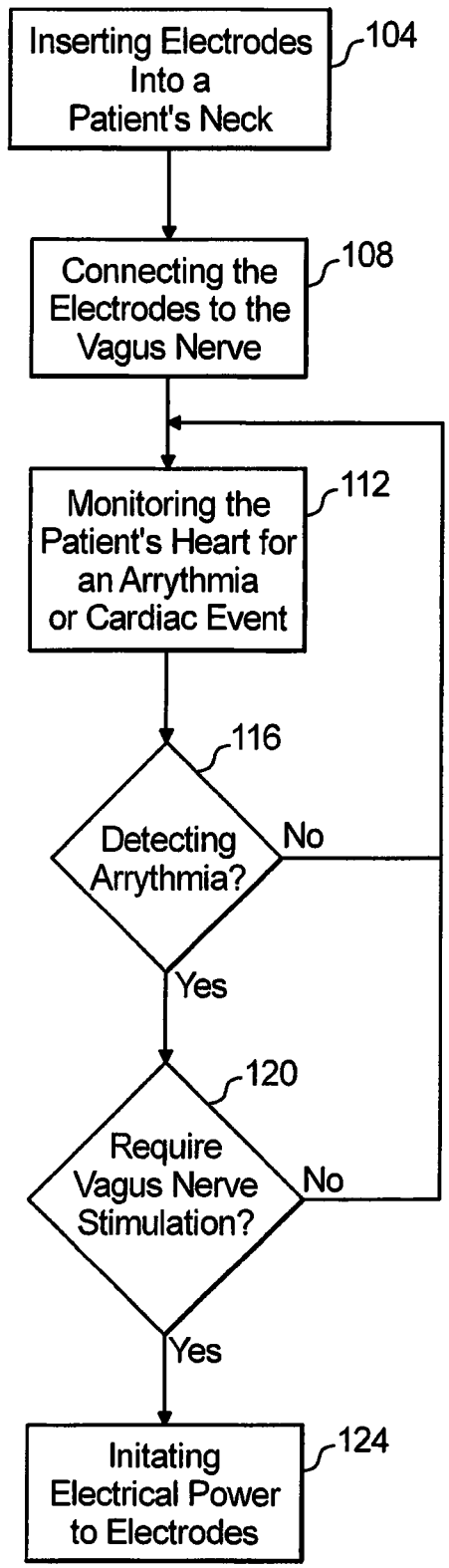
FIG. 2 is flow chart of a method according to an embodiment of the invention for treating cardiac arrhythmias using the system shown in FIG. 1.

Referring to FIGS. 1 and 2, a method 100 for treating cardiac arrhythmias suffered by the patient 14 includes the step 104 of inserting the electrodes 18 into a patient's neck 15, and the step 108 of connecting the electrodes 18 to the vagus nerve 30 in the patient's neck 15. Step 112 includes monitoring the patient's heart for a cardiac arrhythmia or a specified cardiac event. Step 116 including answering whether a cardiac arrhythmia is detected in step 112. If an arrhythmia is not detected the method 100 continues to monitor the heart at step 112. If an arrhythmia is detected the method continues to step 120 to determine if the arrhythmia detected requires vagus nerve stimulation to remedy the arrhythmia. If the arrhythmia is determined not to require vagus nerve stimulation, the method 100 returns to step 112 to monitor the heart of the patient. If the arrhythmia requires vagus nerve stimulation in step 120, the method 100 proceeds to step 124 to automatically initiate electrical power to the electrodes power source 50, thereby applying electrical stimulation to the vagus nerve 30. The controller 40 may monitor the heart and automatically initiate vagus nerve stimulation as will be explained in greater detail below referring to FIG. 9.

The method 100 for treating cardiac arrhythmias according to an embodiment of the invention includes inserting electrodes into a patient's neck area for connection to the vagus nerve. Accessing the vagus nerve via the neck of the patient can be achieved by making a superficial incision in the vicinity of the trachea to expose the vagus nerves. Connection to the vagus nerves may be achieved by using connection elements 32.

The application of the electrical stimulation may be continued to produce and maintain a brief period of cardiac standstill. The period of cardiac standstill may last from about 1-2 seconds, and in some instances can be longer. In the method 100 according to the present invention, the stimulation of the vagus nerve is implemented exclusively, that is, no other cardiac electrical stimulation is used. The electrical current supplied to the electrodes and applied to the vagus nerve may be in the range of 1.0 to 5.0 mA (milliamperes), or sufficient to activate vagal efferent fibers. The electrical current may be applied to the vagus nerve using the electrodes using a series of brief electric pulses (pulse train) lasting less than 20 seconds. The pulse train may be about 20-50 Hz. The pulse train may provide a short period of desirable cardiac standstill. The system and method described herein may initiate the electrical stimulation using the electrodes to the vagus nerve automatically when a specified cardiac event is detected, such as ventricular fibrillation.

Vagus nerve stimulation applied specifically in response to a fibrillation episode can be used to safely defibrillate a fibrillating heart. In the embodiment of the present invention, the method 100 and system 10 for treating cardiac arrhythmias includes using a vagal nerve stimulator device including electrodes 18 to effect defibrillation of the heart via a safer, less invasive procedure. The stimulator or stimulator device may be embodied as the electrodes 18, the controller 40, and the electrical power source 50, shown in FIG. 1. The vagus nerve may be surgically accessed via the neck (in one example, cervically) with devices which can be used to stimulate the nerve. High intensity stimulus of the vagus nerve is needed to activate the efferent nerve fibers which send signals to organs, in this case, the heart. The method and system disclosed herein is envisioned to include the modification of modified designs, controls, and uses of vagal nerve stimulators such that effective defibrillating pulses can be delivered. The method and system of the present invention provides heart defibrillation which only requires minor surgical access to the vagus nerve in the neck, and therefore provides similar benefits but with significantly less risk of surgical complications or direct cardiac and vascular damage of more invasive methods. Thereby, the method and system of the present invention provides a treatment for cardiac arrhythmias, including ventricular fibrillation, which includes vagus nerve stimulation, for example high frequency vagus nerve stimulation, used on its own, that is, without any other forms of stimulation for defibrillation of the heart.

When particularly directed to ventricular fibrillation, the method 100 according to the embodiment of the present invention includes a stimulation protocol for use with a vagus nerve stimulator, including the electrodes 18 as shown in FIG. 1, to prevent or stop ventricular fibrillation. The vagus nerve stimulation can convert ventricular fibrillation to a normal cardiac rhythm with a short train of high frequency stimulus pulses, for example, 20-100 Hz (Hertz) (or cycles per second), and in another example 50 Hz (Hertz) (or cycles per second), which is sufficient to induce a brief period of cardiac standstill. A brief train of pulses may be sufficient to produce a period of cardiac standstill, resulting in cardioversion. The stimulator can be "off" until it needs to be activated in response to ventricular fibrillation (VF) or other arrhythmia. Upon activation, a brief train of stimulus pulses (<20 seconds) can cardiovert. The prescribing physician may also elect to deliver a low frequency continuous train of vagus nerve stimuli to provide protection of the heart from arrhythmias. The continuous train of vagus nerve stimulation can be sufficient to stimulate the nerve, for example, lower intensity stimulation for nerve fiber activation (afferent) to the brain, and high intensity stimulation for nerve fiber activation from the brain (efferent) to the heart. The range of stimulation may be set based on the physiology of the patient, that is, the patient's individual needs. Brief trains or continuous trains of afferent vagal nerve fiber activation are not known to be harmful, and are sometimes used clinically as anti-convulsant or anti-depressant treatments.

A configuration step may be added to the method of the present disclosure, which may use five to ten pulses per second to cause one or two missed heart beats. Thereby, the configuration step is not life threatening, and has minimal discomfort to the patient.

In another embodiment of the invention, electrodes for electrocardiogram (ECG) can be directly incorporated into the vagal implant.

Advantages of the method and system according to the present invention include that no electrodes enter the heart. Also, the short trains of efferent activity necessary for cardioversion have will have no detriment physiologically from either the activation of afferent fibers or the activation of vagal efferents to other organs. Further, risk of adverse effects on the heart such as irritation and bleeding of blood vessels are eliminated with the present system and method as the implantable electrodes do not require access to a blood vessel. Further, irritation of the ventricular lining and the valve edges can lead to complications that will not occur from an entirely extra-cardiac device such as the system 10 of the present invention.

Additionally, in the present method and system, vagus nerve stimulation parameters can be set to produce a short period of cardiac standstill (the equivalent of one or two missed beats), and the train length extended or repeated trains given with the safe understanding that the longer trains or repeated trains will be effective for cardioversion when necessary. The method and system of the present invention can be configured to deliver a low frequency train of vagal stimuli, which will offer protection from fibrillation in some patients. Patients with vagus nerve stimulators implanted for seizure control cannot be cardioverted with conventional methods. The method 100 and system 10 for defibrillation has a number of advantages over existing implantable technologies. For example, while it requires surgery for placement of the electrodes on vagus nerve, no electrodes enter the heart. Second, the stimulus parameters can be configured and tested much more simply, and safely.

Vagus nerve stimulation parameters can be set to produce a short period of cardiac standstill (the equivalent of one or two missed beats), and the train length extended with the safe understanding that the longer trains will be effective. Therefore, vagus stimulation can be used not just to decrease the risk of fibrillation or as a defibrillation adjunct, but it can be used a true defibrillator.

In an alternative embodiment, the method and system of the present invention could be incorporated with the vagus nerve stimulation used for anticonvulsant purposes, i.e., the device would be configured to deliver a low intensity stimulus for selective afferent activation as seizure therapy, and a higher intensity stimulus for efferent activation as cardioversion.

Experiment Methods

In an example of the present method and system using rats, each animal was anesthetized with urethane (Sigma™, St. Louis, Mo.) at 1.5 g/kg ip and supplemented as necessary with 0.1 g/kg ip. The rats were subsequently moved to a warming pad to maintain body temperature and then prepared for surgery.

A single superficial incision was made along the length of the rat's sternohyoid muscle and the trachea was exposed by making an opening along the fibers of the muscle. After making an incision beneath one of the rings of the trachea, an endotracheal tube was inserted into the trachea and tied in place with suture. Both vagus nerves were dissected, and a custom-made electrode was placed along one of the nerves for stimulation. The nerves were protected from drying with paraffin oil. Continuous blood pressure (BP) recordings were made from an arterial catheter (polyethylene tubing, cut square, 0.5 mm inside diameter, 0.8 mm outside diameter) in the femoral artery that was connected to a blood pressure transducer. Copper bands coated with conductive gel were placed over the rat's wrists and an ankle for EKG recordings. All signals except for the BP signal were amplified and filtered to pass 1 Hz to 1 kHz. All signals were subsequently digitized at 2 kHz and stored to disk for analysis. A subset of animals had echo cardiographic recordings taken during VF and defibrillation. Ventricular fibrillation was induced by a variety of methods. The first included bilateral vagotomy, administration of 2-16 mg/kg intra-arterial isoproterenol, and a period of hypoxia by placing a 3-6 ml tube over the endotracheal tube. Another was accomplished by direct electrical stimulation of the cardiac ventricles. A third method used intra-arterial infusion of 3 M potassium chloride which produced ventricular tachyarrhythmias. Lastly, aconitine (50 mg/kg intra-arterial) was infused until VF was elicited. Vagus nerve and cardiac stimulation were performed using an isolated pulse stimulator attached to the electrodes on one of the nerves or touching the heart, respectively. For VNS, biphasic current pulses (1-9.8 mA) that lasted for 1-millisecond were passed as 20 or 50 Hz trains for periods of 0.5-20 seconds. For cardiac electrical stimulation, biphasic current pulses (2-10 mA) that lasted for 4-6.5 milliseconds were passed as a 20 or 50 Hz train for a period of 4 seconds. Efficacy of VNS defibrillation was assessed when blocking the effects of the neurotransmitters nitric oxide (NO) and acetylcholine. A subset of rats that underwent VF by direct cardiac electrical stimulation or autonomic activation/hypoxia was administered L-NG Nitroarginine methyl ester (L-NAME; 27 mg/kg, intra-arterial) and VNS defibrillation efficacy was tested. The rats received atropine (5 mg/kg intraarterial) in addition and the rats were tested again.

Recordings were reviewed using scripts written in Matlab™. VNS defibrillation was recorded as successful when it brought VF to cardiac standstill with subsequent sinus rhythm after stimulus termination. It was recorded as unsuccessful if VF terminated by itself at a point in time after the stimulus terminated. Statistical tests were done by performing one-way ANOVA, and post-hoc tests are reported with Tukey's 95% confidence interval.

Results

Defibrillation Via Vagus Nerve Stimulation

The results for vagus nerve stimulation wherein a total of 48 rats were used in the experiments are described below. To induce ventricular fibrillation, 23 rats were induced via the autonomic activation/hypoxia protocol given above, 8 rats had their hearts electrically stimulated, 17 rats were infused with KCL (ventricular tachyarrhythmia), and 3 rats were infused with aconitine. Fifteen of the rats given KCL and one of the rats given aconitine had also been tested with the autonomic activation/hypoxia protocol.

In general, vagus nerve stimulation at 50 Hz with a sufficient current to activate all efferent fibers was able to cause cardiac standstill. Longer stimulus trains were accompanied by ventricular escape beats later in the stimulus train. Stimulation at 20 Hz with the same current more commonly caused a significant slowing of the heart rate and reduced the blood pressure, but did not bring about cardiac standstill.

Of the rats with autonomic activation/hypoxia-induced ventricular fibrillation. Trains greater than or equal to 1.5 seconds were necessary to defibrillate. These rats experienced VF 1-4 times per animal. Counting episodes of VF, 85.7% of the total fibrillation count across all stimulation conditions (30/35 in 23 rats) were defibrillated successfully in these animals. The conditions of stimulation ranged in current from 1 to 4.5 mA at 50 Hz and length of trains from 0.5 to 20 seconds. Across all conditions, a total of 1.1+/−0.3 attempts were required to defibrillate successfully. The heart was brought to cardiac standstill during the defibrillatory period, although some ventricular beats occurred after defibrillation shown in chart 200 (see FIG. 3). Of the animals that experienced any period of cardiac standstill during VNS, all 30/30 VF episodes were defibrillated.

Figure 3:
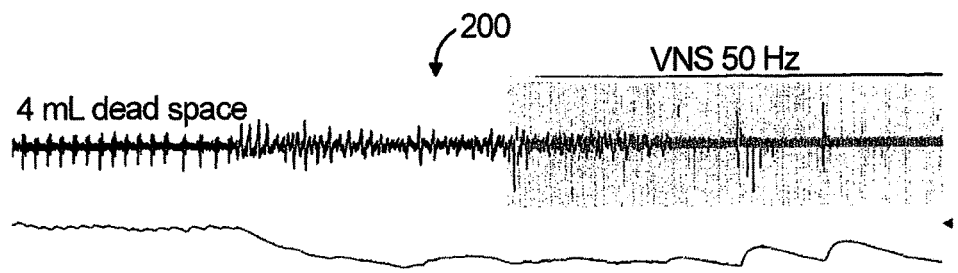
FIG. 3 is a graph showing heart activity during a defibrillation period of a test using animals.
Figure 4:
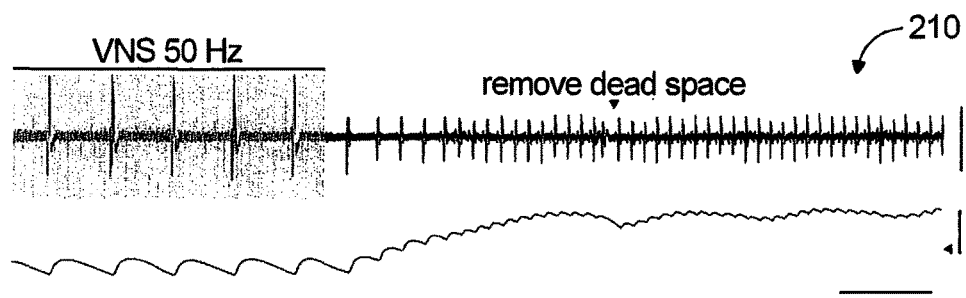
FIG. 4 is a continuation of the graph shown in FIG. 3 showing heart activity during fibrillation/defibrillation in the test.

Referring to FIGS. 3 and 4, the graphs 200, 210 depict EKG and BP tracings for a rat that underwent autonomic activational hypoxia induced VF and VNS defibrillation are shown. The rat was infused with isoproterenol 26 mg/kg. Four mL of dead space tubing were placed over the endotracheal tube for 38 seconds before fibrillation. In both FIGS. 3 and 4, the right vagus was stimulated with 3.5 mA, 1-millisecond pulses at 50 Hz to defibrillate.

Twelve animals underwent echocardiographic imaging during fibrillation/defibrillation to assess the changes in cardiac wall movement shown in chart 210 (see FIG. 4). The walls of the left ventricle were found to move erratically during fibrillation, though with an amplitude less than that of normal beats. VNS defibrillation caused the walls of the heart to stop moving completely during stimulation until escape beats appeared.

Rats that underwent direct cardiac stimulation had episodes of VF induced 1-9 times per animal. A feature of the VF the rats experienced was that in the recordings it was more than twice the amplitude of the VF experienced by rats that underwent the autonomic activation/hypoxia protocol. Of the total number of VF episodes they experienced across all stimulation conditions, 78.4% (29/37) were defibrillated by VNS. The conditions of the VNS stimulations ranged from 2.75 to 9.8 mA with 20 or 50 Hz trains that lasted 3 seconds in duration. When limiting the count to only animals that were stimulated with 50 Hz trains (including all stimulus intensities), VNS defibrillation had an 88.9% (16/18)

success rate with only 1.5+/−0.8 attempts. Of the animals that experienced any period of cardiac standstill during VNS, all 29/29 VF episodes were defibrillated. Successful defibrillation elicited a period of cardiac standstill before returning to sinus rhythm, as shown in charts 220 and 230 shown in FIGS. 5 and 6.

Figure 5:
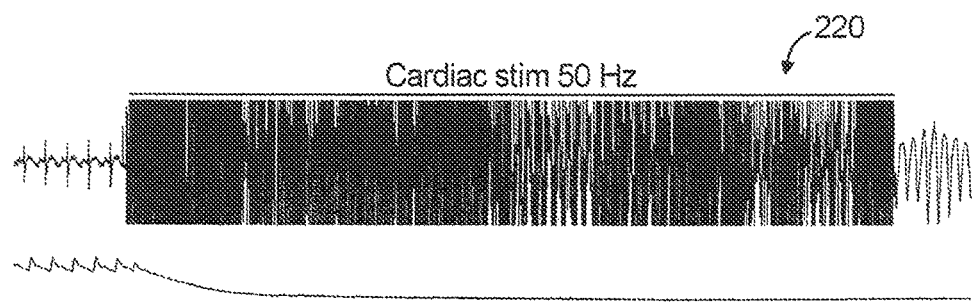
FIG. 5 is a graph showing heart activity during fibrillation/defibrillation after direct cardiac stimulation in the test.
Figure 6:
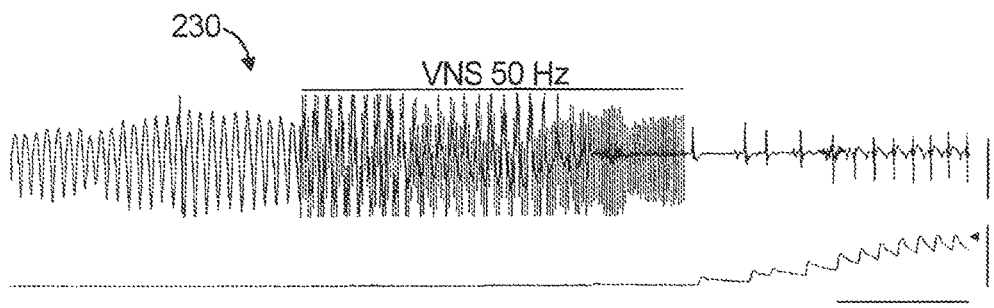
FIG. 6 is a continuation of the graph shown in FIG. 5 showing heart activity during fibrillation/defibrillation after direct cardiac stimulation in the test.

Referring to FIGS. 5 and 6, graphs 220, 230 depict EKG and BP tracings of a rat that underwent VF and VNS defibrillation after direct electrical cardiac stimulation. Cardiac stimulation was performed by stimulating the ventricles with 4 mA, 4-millisecond pulses at 50 Hz. Defibrillation was accomplished by stimulating the left vagus with 4 mA, 1-millisecond pulses at 50 Hz.

In pooling the above sets of VF episodes from all rats, left vs. right vagus nerve stimulation efficacy was compared. A total of 25 rats had left VNS and 5 rats had right VNS, for a total of 30 animals. It was found that, there were no statistically significant differences in efficacy of right vs. left vagus stimulation. None of the 17 rats infused with KCL had their ventricular tachyarrhythmias stopped by VNS. A range of stimulation intensities (1 to 4.5 mA) and train durations (3 to 20 seconds) were attempted, but KCL rendered VNS ineffective to bring about any conversion. The ventricular fibrillations arising in the 3 rats infused with aconitine could not be brought to cardiac stand still either, neither with a range of currents (1 to 4.5 mA) nor a range of train durations (3 to 20 seconds). In the above case, both KCL and aconitine interfered with the action of the vagus nerve.

Neurotransmitter Basis of Defibrillation by VNS

As both nitric oxide (NO) and acetylcholine have been shown to be the neurotransmitters responsible for vagus nerve action, testing of whether vagus nerve stimulation could defibrillate with the same potency when the action of these neurotransmitters was blocked was conducted. Four rats that underwent cardiac stimulation and 3 rats that underwent autonomic activation/hypoxia-induced fibrillation were also infused with either L-NAME alone or with LNAME and atropine and had more fibrillations induced. The results from these animals were pooled together.

VNS was done at a variety of currents (3 to 9.8 mA) and train durations (3 to 5 seconds) at 20 or 50 Hz. Among the rats treated with L-NAME, 94%+/−14 (n=6) were successfully defibrillated as shown in graph 240 shown in FIG. 7, and among the rats treated with L-NAME and atropine, 31%+/−29 (n=5) were defibrillated as shown in graph 250 shown in FIG. 8. Comparison with the 81%+/−32 (n=24) of successful defibrillations in animals shows a statistical difference among the groups (p=0.004). Post-hoc tests showed no difference between control animals and animals with L-NAME, but a difference between these two groups and those animals with L-NAME and atropine.

Figure 7:
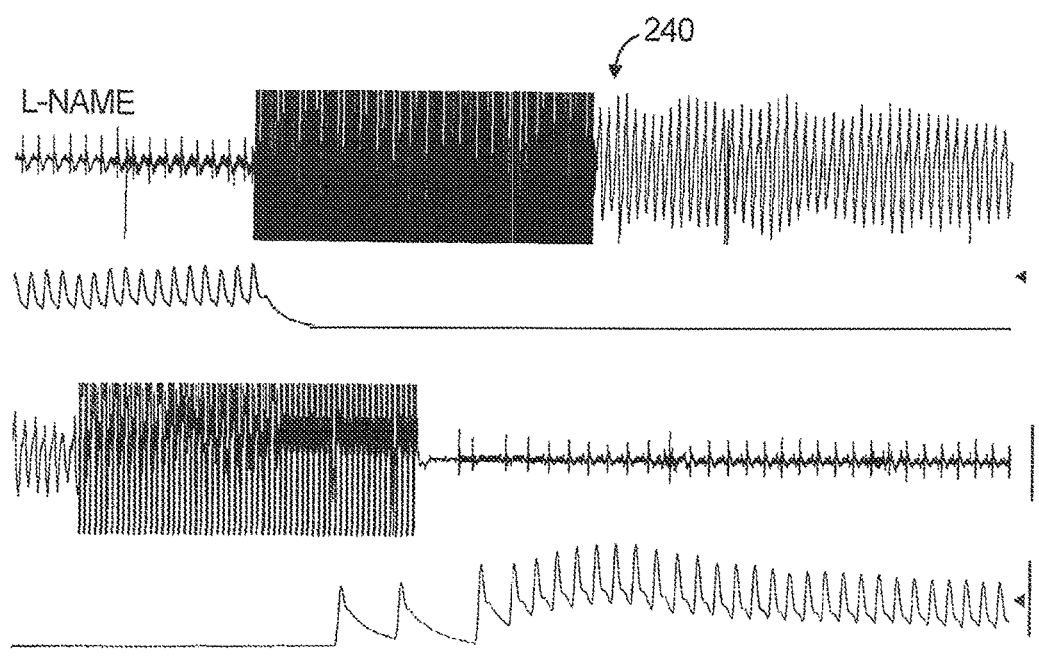
FIG. 7 is a graph showing heart activity during fibrillation/defibrillation after direct cardiac stimulation in the test.
Figure 8:
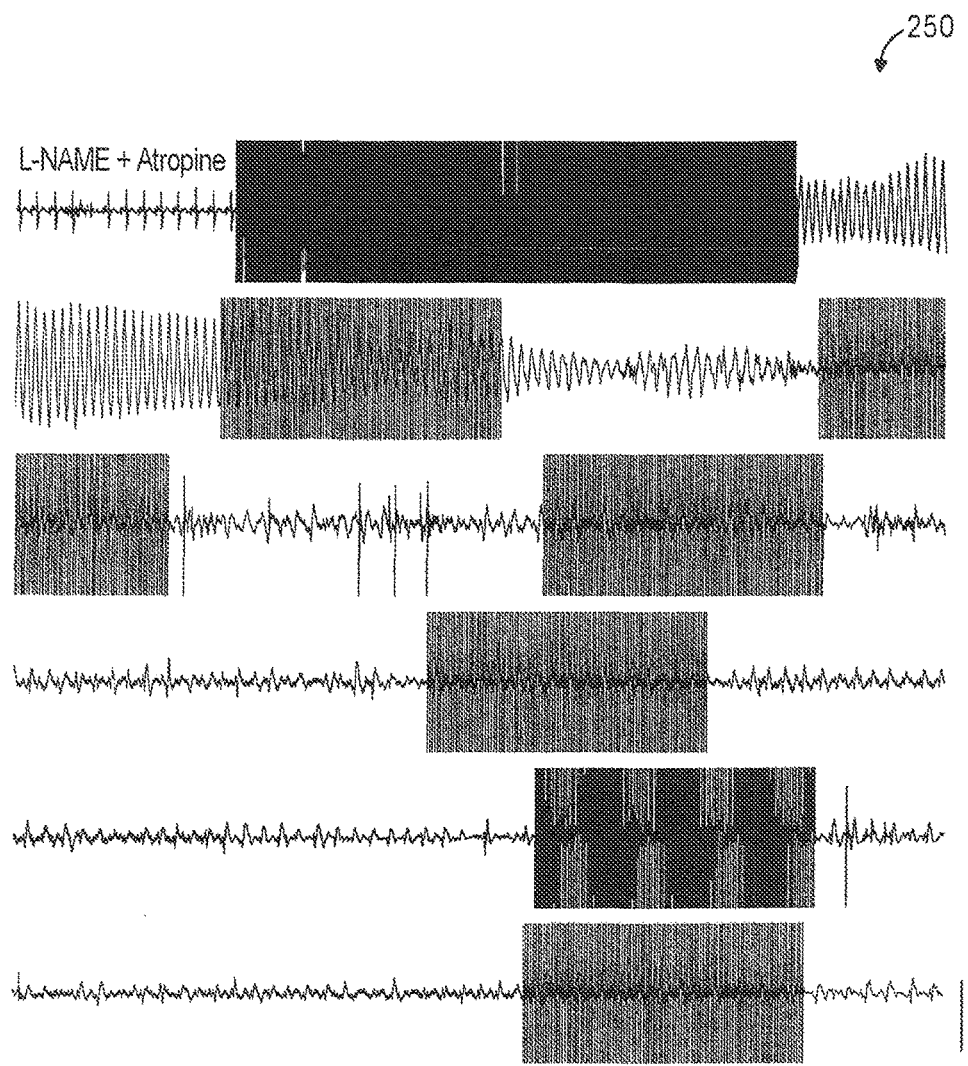
FIG. 8 is a graph showing heart activity during fibrillation/defibrillation after direct cardiac stimulation for a rat infused with L-NAME and atropine showing VNS defibrillation was ineffective in the test.

Referring to FIGS. 7 and 8, graphs 240, 250 depict EKG and BP tracings from a rat infused with L-NAME 27 mg/kg that underwent VF and VNS defibrillation after direct cardiac stimulation are shown in graph 240. In a different rat infused with L-NAME 27 mg/kg and atropine 5 mg/kg, VNS defibrillation was ineffective in graph 250. In both examples, cardiac stimulation was performed by stimulating the ventricles with 4 mA, 4-millisecond pulses at 50 Hz. Defibrillation was accomplished by stimulating the left vagus with 4 mA, 1-millisecond pulses at 50 Hz.

Discussion of Experiment Results

Right and left VNS appear to have similar VNS efficacy rates. VNS is ineffective at converting rhythm for animals that underwent KCL infusions, since the high concentration of potassium likely rendered vagus nerve action ineffective. In addition, it could not defibrillate in the presence of aconitine, a drug that also interferes with nerve function by poisoning voltage-sensitive sodium channels. Lastly, VNS had the ability to defibrillate even when blocking NO signaling with L-NAME, though it was much less effective when atropine was administered. Therefore, vagus stimulation can be used not just to decrease the risk of fibrillation or as a defibrillation adjunct, but it can be used a true defibrillator.

Defibrillation by existing devices (both internal and external) function by completely depolarizing membranes of the cardiac myocytes, specifically during the relative refractory period. Large electric shocks are most effective at defibrillating, though rapid pacing (e.g., 170/min) can also be used to entrain the area of the heart especially during ventricular tachycardia. However, electric cardioversion may also play a role in nearby nerve-altering activity, as one study has shown sustained sympathetic attenuation in anesthetized dogs after high-energy shocks.

VNS has been used for a variety of conditions, including epilepsy, depression, and heart failure. Because there is risk in delivering large external electrical shocks to such patients, VNS can be used as a defibrillator in those with existing implanted vagus nerve stimulators. Current implantable cardioverter-defibrillators are reported to have perfect or nearly perfect efficacy given sufficiently high current. The defibrillation method described here was perfectly effective when VNS was configured to produce a period of cardiac standstill. Of the rats studied, one rat died from VF, and this rat had been administered L-NAME and atropine, which rendered VNS ineffective. Thus, VNS is highly effective as a defibrillator provided it is configured to produce cardiac standstill, and this configuration can be safely established at the time of implant and checked routinely for consistency.

Figure 9:
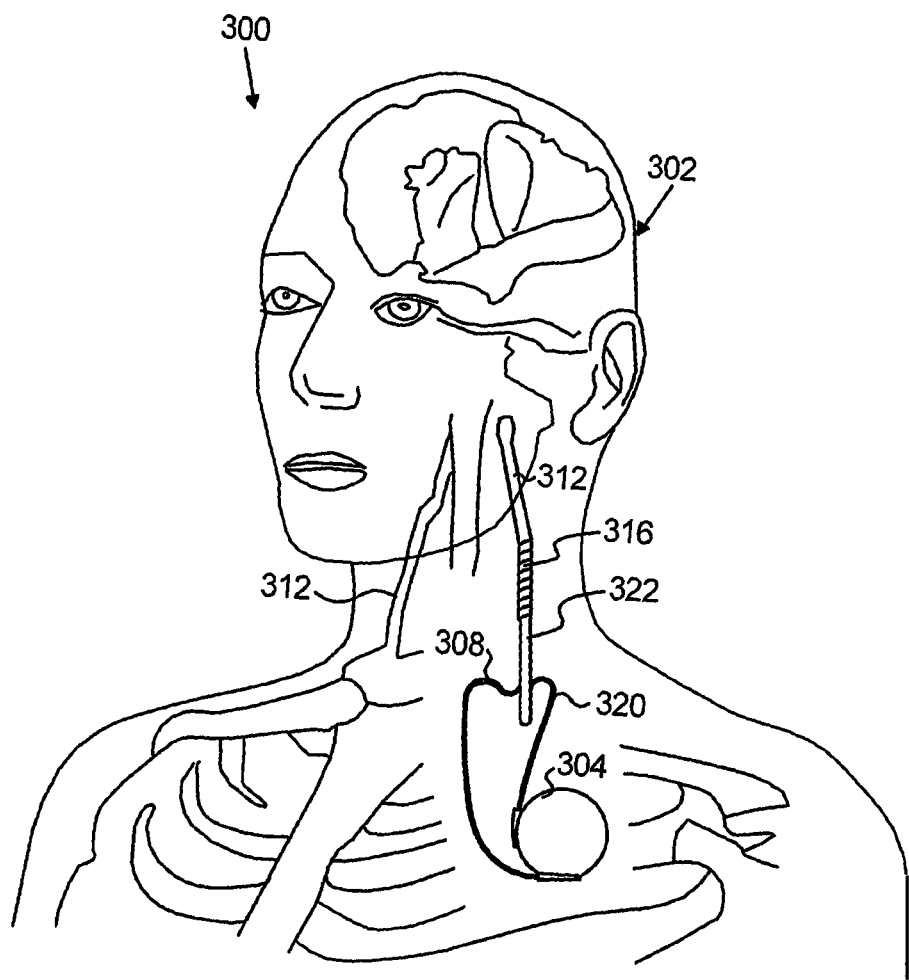
FIG. 9 is a isometric view of a system according to the invention for implanting a pulse generator device in a patient.
Figure 11:
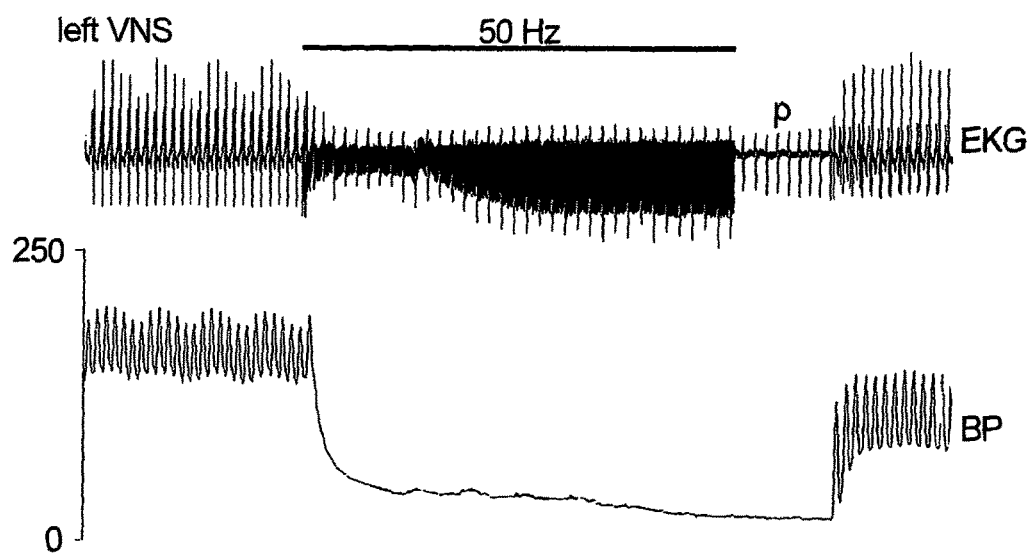
FIG. 11 is a graph showing pig heart activity during left VNS.
Figure 12:
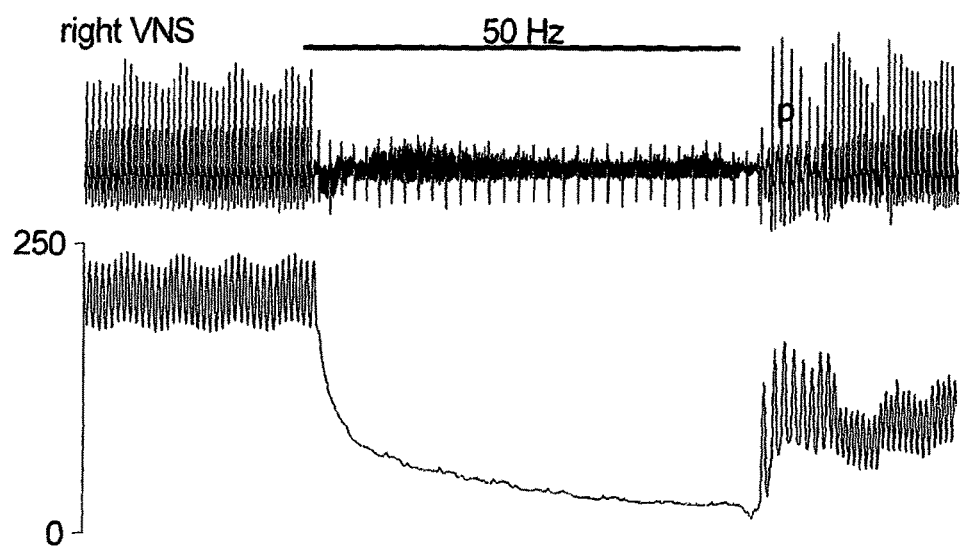
FIG. 12 is a graph showing pig heart activity during right VNS.
Figure 13:
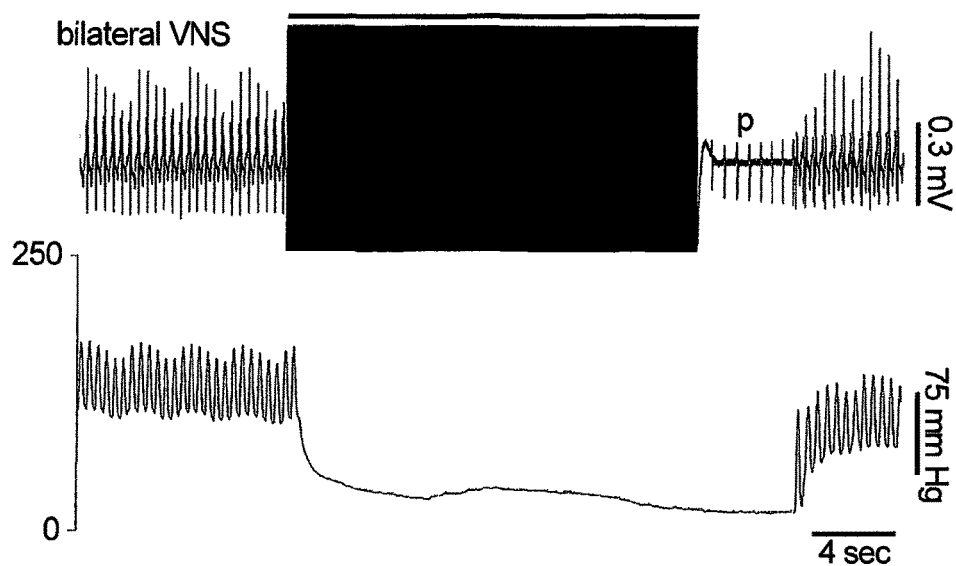
FIG. 13 is a graph showing pig heart activity during bilateral (right and left) VNS.
Figure 14:
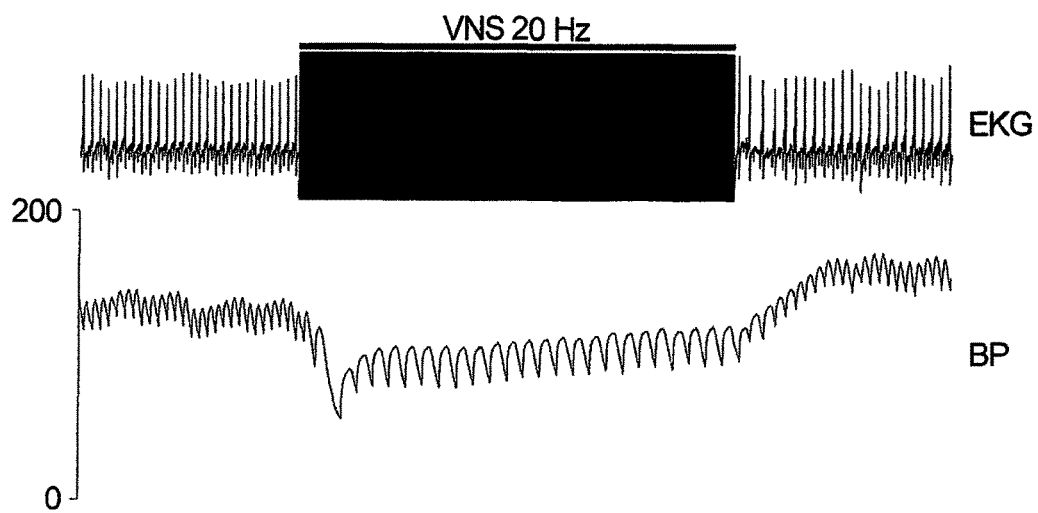
FIG. 14 is a graph showing pig heart activity during bilateral VNS administered at 20 Hz.
Figure 15:
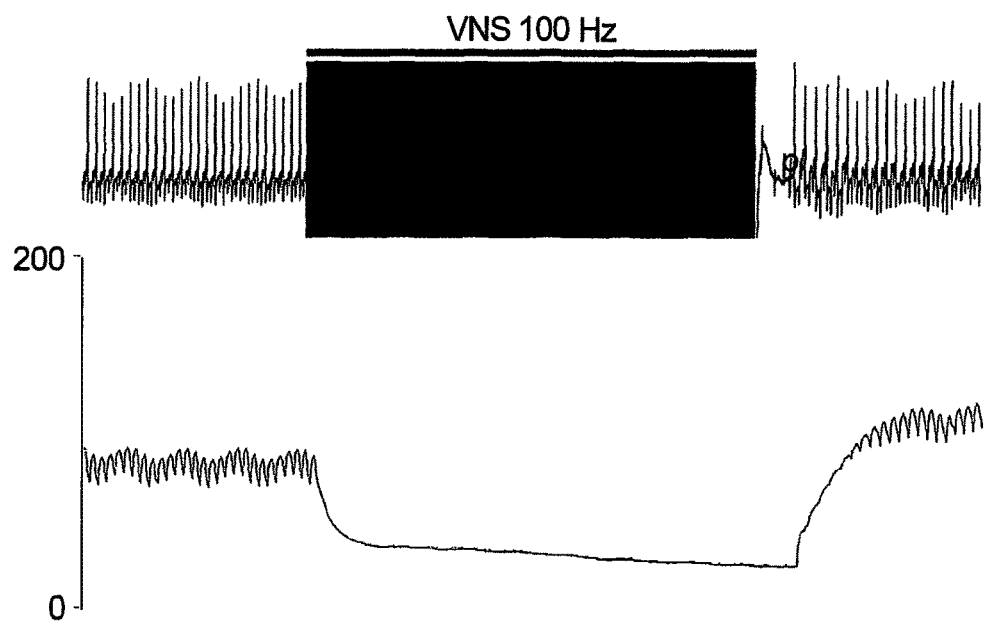
FIG. 15 is a graph showing pig heart activity during bilateral VNS administered at 50 Hz.
Figure 16:
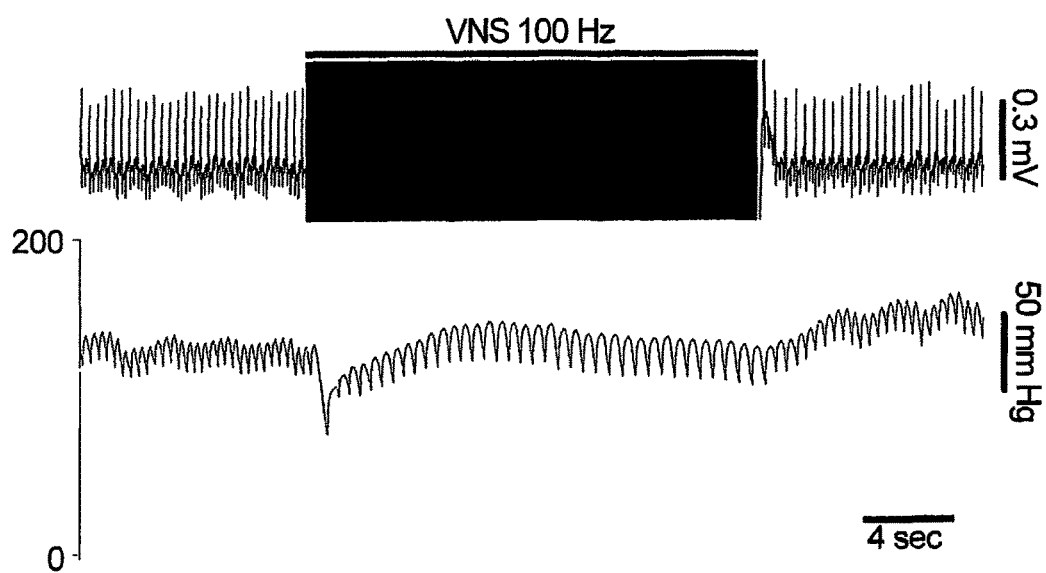
FIG. 16 is a graph showing pig heart activity during bilateral VNS administered at 100 Hz.

Referring to FIG. 9, in an embodiment of the invention, a system 300 for stimulating the vagus nerve includes pulse generator device 304 (also referred to as a vagus nerve stimulation device). The system 300 contemplates a surgeon first making an incision along the outer side of the chest of a patient 302 on the left side of the patient's chest. The pulse generator device 304 is implanted under the skin of the patient. A second incision may be made horizontally in the lower neck, along a crease of skin. A wire 308 from the device 304 has electrodes 316 at a distal end thereof. The electrodes 316 are wound around the vagus nerve 312 in the left side of the neck. The brain of the patient is not involved in the surgery. The device 304, may be, for example, a flat, round battery, about an inch and a half (4 cm) across, and 10 to 13 millimeters thick, with variation depending on the model used, and smaller models being readily usable. In one example, the implantation procedure of the device 304 can last about 50 to 90 minutes with the patient under general anesthesia, or a hospital stay of one night may be required. Alternatively, a surgeon may perform the procedure with local anesthesia and the patient can be discharged the same day. Alternatively, a second set of electrodes may be attached to a second vagus nerve, thus providing stimulation to both vagus nerves routinely or when necessary. In one embodiment, one vagus nerve can be stimulated. In another embodiment, both vagus nerves can be stimulated.

In the system 300, the device 304 is also connected to the vagus nerve using wire 320 with distal recording electrodes 322 coupled to the vagus nerve 312. The recording electrodes 322 provide an EKG of the heart using their vagus nerve connection. Thereby, the device 304 is able to sense the heart's electrical activity, for example, by monitoring the heart using an EKG, and initiate vagal nerve stimulation using the device 304 as shown in FIG. 9. The vagus nerve 312 stimulation occurs during arrhythmia of the heart (e.g., fibrillation, ventricular fibrillation, or ventricular tachycardia), and the vagus nerve 312 stimulation reverses the arrhythmia (i.e., reverses the fibrillation or ventricular fibrillation).

Using the device 304 in the system 300, an electrophysiologist may program the strength and timing of the impulses according to each patient's individual needs. The settings can be programmed and changed without entering the body. The electrophysiologist may use a programming wand connected to a laptop computer. The programming wand and the device may be programmed by a neurologist or other appropriate specialist. For all patients, the device is programmed to go on for a certain period of time, for example, 7 seconds or 30 seconds, and then to go off for another period of time, for example, 14 seconds or 5 minutes. The device may run continuously, usually with 30 seconds of stimulation alternating with 5 minutes of no stimulation. The patient is usually not aware that it is operating. Further, the present device eliminates painful shocks as in known treatments, as well as eliminating their physiological effects. Further, the device provides a protective feature, that is, preventing heart arrhythmias, including those protective features in current ICD devices.

Large Animal Tests

In large animal testing of the present invention, 8 pigs and 10 sheep were anesthetized with urethane 1 g/kg intravenously and placed on a ventilator. Platinum electrodes were wrapped around the vagus nerves. Limb-lead electrocardiogram and carotid blood pressure recordings were made. VNS was performed in animals with 1-millisecond pulses at 1, 2, 5, 10, 20, 50, and 100 Hz. Potency of VNS was evaluated by counting the number of beats during stimulation. Ventricular fibrillation (VF) was produced by opening the thorax and applying direct current to the ventricles. Epicardial echocardiography was performed during sinus rhythm, VNS, and during VF for three periods—before, during, and after VNS.

FIG. 11 through FIG. 18 provide graphical representations of the results of the large animal testing. FIG. 19 provides a comparison of the results found in the above described testing in rats against the results found in the large animal testing of pigs and sheep.

Figure 17:
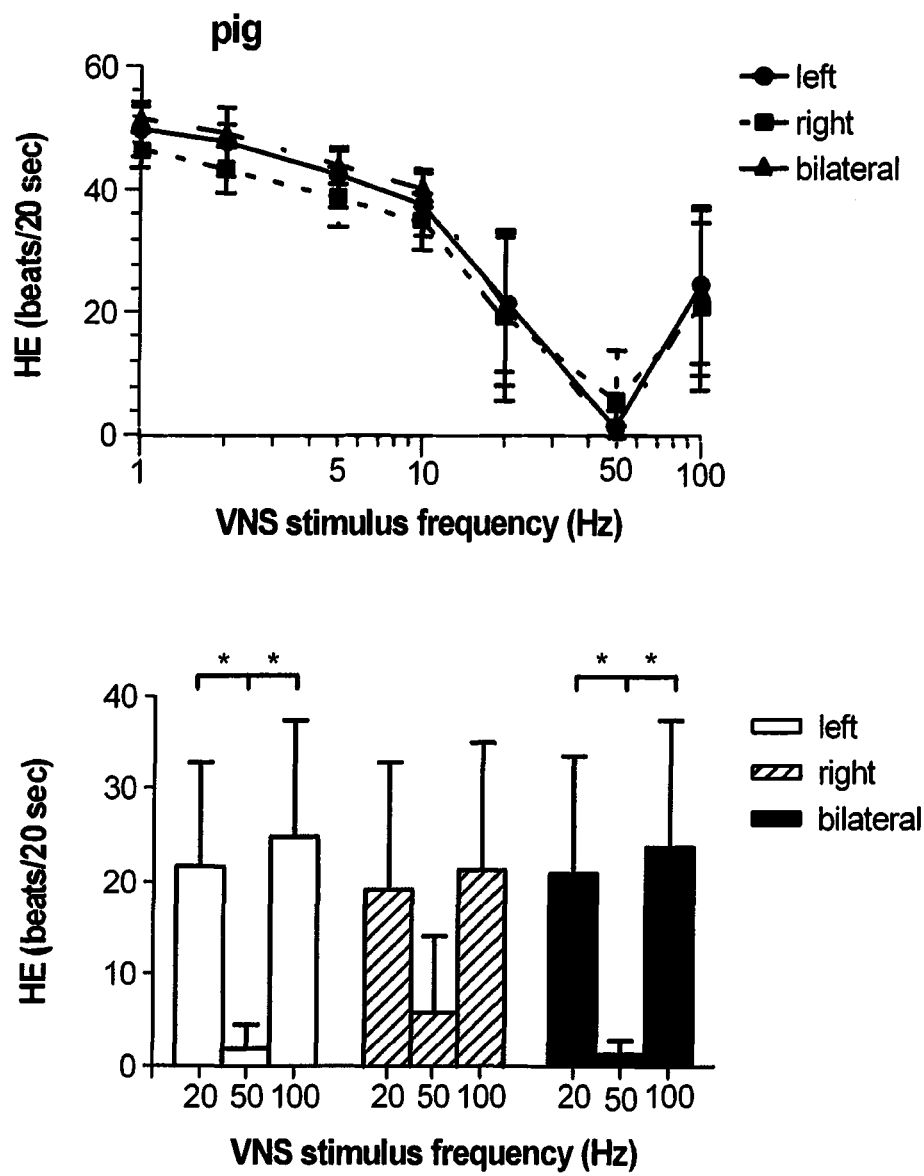
FIG. 17 shows compiled results of right, left and bilateral VNS on pigs at various frequencies.
Figure 18:
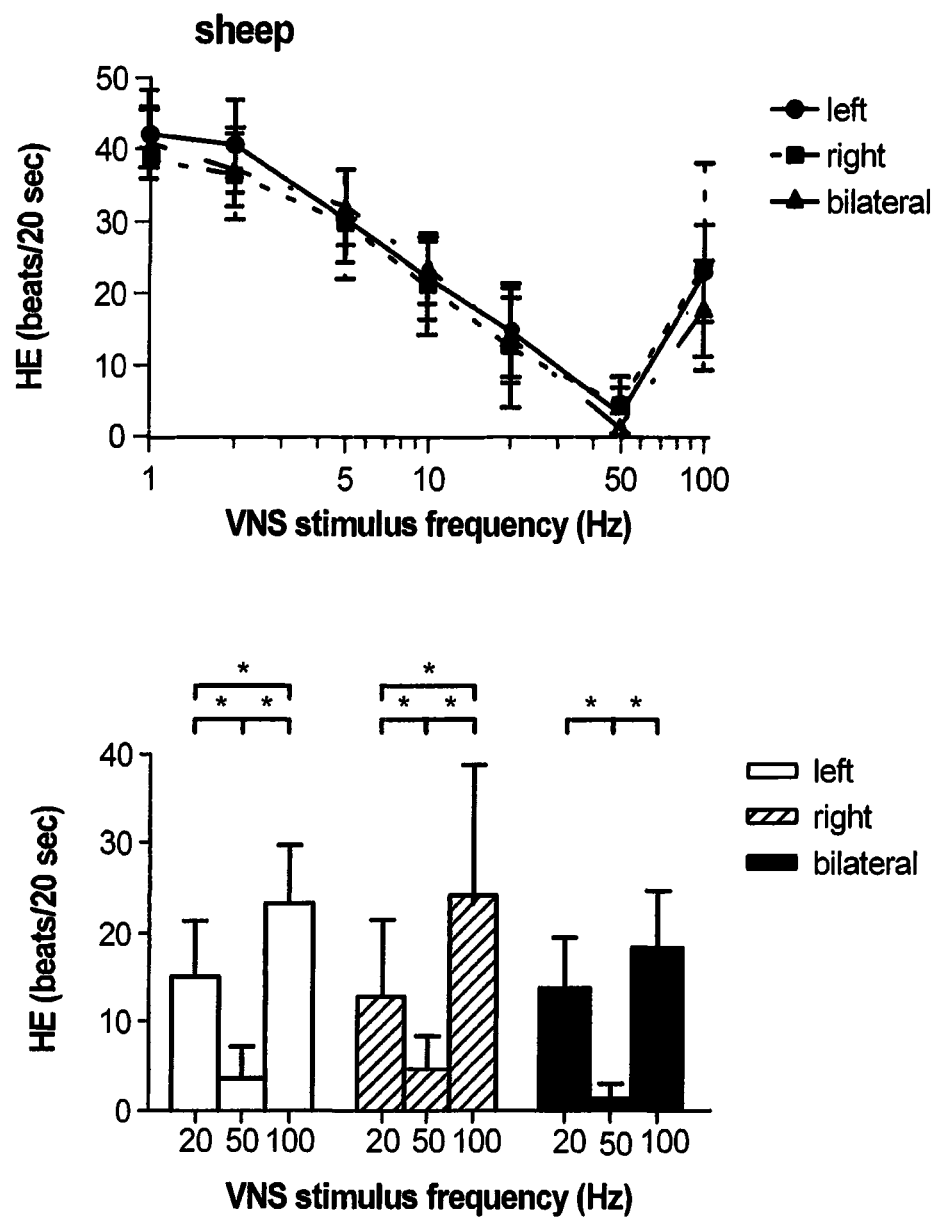
FIG. 18 shows compiled results of right, left and bilateral VNS on sheep at various frequencies.
Figure 19:
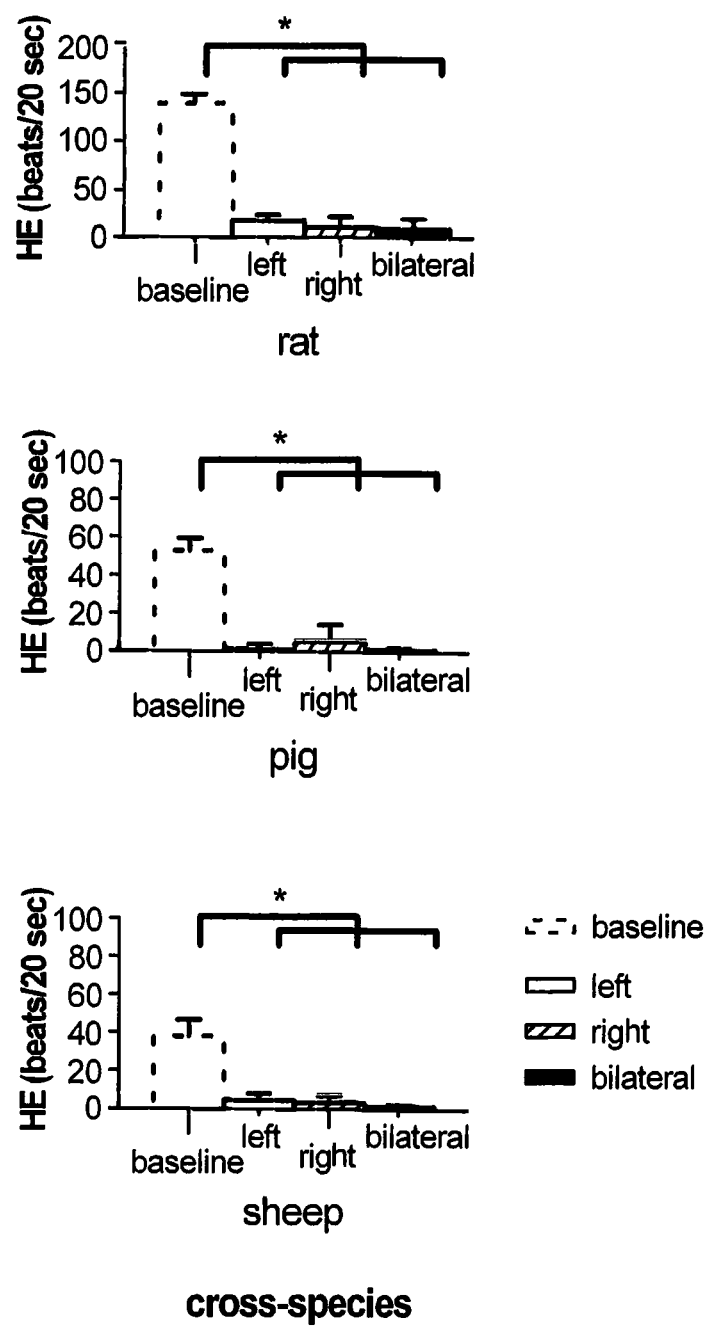
FIG. 19 shows comparative results of right, left and bilateral VNS on rats, pigs and sheep at 50 Hz.

In FIG. 17-19, the bars denoted by asterisks indicate that linked data bars are statistically different from each other. For example, in FIG. 17 the first bar is significantly larger than the middle bar and the middle bar is significantly smaller than the 3rd bar. In FIG. 19 the first bar is significantly different from each of the other 3 bars. Significance is <0.05 for a p value.

As can be seen in the graphs presented in FIG. 19, the results of the VNS testing performed on pigs and sheep closely correspond to the results found in VNS testing on rats. Consequently, strong evidence is present that a similar effect will be seen when the VNS defibrillation method of the present invention is applied to a human patient. Moreover, the large animal testing shows that VNS administered at 50 Hz results in cardiac stand still, in agreement with the findings in the above described rat VNS tests.

While the present invention has been particularly shown and described with respect to preferred embodiments thereof, it will be understood by those skilled in the art that changes in forms and details may be made without departing from the spirit and scope of the present application. It is therefore intended that the present invention not be limited to the exact forms and details described and illustrated herein, but falls within the scope of the appended claims.

What is claimed is:

1. A method for treating cardiac arrhythmias, comprising:
inserting an electrode into a patient's neck;
connecting the electrode to a vagus nerve in the patient's neck;
detecting a cardiac arrhythmia; and
initiating electrical power to the electrode using a controller connected to an electrical power source to apply electrical stimulation to the vagus nerve when a cardiac arrhythmia is detected during a cardiac arrhythmia, wherein no cardiac electrical stimulation is applied, wherein the electrode is configured to apply electrical stimulation to the vagus nerve during ventricular tachycardia or ventricular fibrillation.

2. The method of claim 1, wherein the step of applying the electrical stimulation is continued to produce and maintain a cardiac standstill for a specified period of time and then the electrical stimulation is stopped.

3. The method of claim 2, wherein the cardiac standstill is maintained for at least 2 seconds.

4. The method of claim 1, wherein an electrical current is applied to the vagus nerve using the electrode, the electrical current being in the range of 10 to 100 Hz (Hertz).

5. The method of claim 1, wherein pulses of electrical current are applied to the vagus nerve using the electrode for less than about 30 seconds.

6. The method of claim 1, wherein the electrical stimulation is initiated automatically when a specified cardiac event is detected.

7. The method of claim 1, wherein the controller is configured to convert ventricular tachycardia or ventricular fibrillation to normal cardiac rhythm.

8. A system for treating cardiac arrhythmias, comprising:
an electrode having a distal end insertable into a patient's neck and connectable at a distal end to a vagus nerve;
a controller connected to a proximal end of the electrode, wherein the controller is connected to an electrical power source for providing electricity to the electrode for electrically stimulating the vagus nerve, wherein the electrical stimulation to the vagus nerve is applied during a cardiac arrhythmia; and
a cardiac monitoring device configured to sense the heart's electrical activity, wherein no cardiac electrical stimulation is applied, wherein the system is configured to apply electrical stimulation to the vagus nerve during ventricular tachycardia or ventricular fibrillation.

9. The system of claim 8, wherein the application of the electrical stimulation is continued to produce and maintain a cardiac standstill for a specified period of time.

10. The system of claim 9, wherein the cardiac standstill is maintained for at least 2 seconds.

11. The system of claim 8, wherein an electrical current is applied to the vagus nerve using the electrode, the electrical current being in the range of 10 to 100 Hz (Hertz).

12. The system of claim 8, wherein pulses of electrical current are applied to the vagus nerve using the electrode for less than about 30 seconds.

13. The system of claim 8, wherein the electrical stimulation is initiated automatically when a specified cardiac event is detected.

14. The system of claim 8, wherein the controller is configured to convert ventricular tachycardia or ventricular fibrillation to normal cardiac rhythm.

15. A method for treating cardiac arrhythmias, comprising:
inserting two electrodes into a patient's neck;

connecting the electrodes to a vagus nerve in the patient's neck;

detecting a cardiac arrhythmia; and initiating electrical power to the electrodes using a controller connected to an electrical power source to apply electrical stimulation to the vagus nerve when a cardiac arrhythmia is detected during a cardiac arrhythmia, wherein no cardiac electrical stimulation is applied, wherein the electrodes are configured to apply electrical stimulation to the vagus nerve during ventricular tachycardia or ventricular fibrillation.

16. The method of claim 15, wherein the step of applying the electrical stimulation is continued to produce and maintain a cardiac standstill for a specified period of time and then the electrical stimulation is stopped.

17. The method of claim 15, wherein the cardiac standstill is maintained for at least 2 seconds.

18. The method of claim 15, wherein an electrical current is applied to the vagus nerve using the electrodes, the electrical current being in the range of 10 to 100 Hz (Hertz).

19. The method of claim 15, wherein pulses of electrical current are applied to the vagus nerve using the electrode for less than about 30 seconds.

20. The method of claim 15, wherein the electrical stimulation is initiated automatically when a specified cardiac event is detected.

21. The method of claim 15, wherein the controller is configured to convert ventricular tachycardia or ventricular fibrillation to normal cardiac rhythm.

22. A system for treating cardiac arrhythmias, comprising:

two electrodes having a distal end insertable into a patient's neck and connectable at a distal end to a vagus nerve;

a controller connected to a proximal end of the electrodes, wherein the controller is connected to an electrical power source for providing electricity to the electrodes for electrically stimulating the vagus nerve, wherein the electrical stimulation to the vagus nerve is applied during a cardiac arrhythmia; and a cardiac monitoring device configured to sense the heart's electrical activity, wherein no cardiac electrical stimulation is applied, wherein the electrodes are configured to apply electrical stimulation to the vagus nerve during ventricular tachycardia or ventricular fibrillation.

23. The system of claim 22, wherein the application of the electrical stimulation is continued to produce and maintain a cardiac standstill for a specified period of time.

24. The system of claim 22, wherein the cardiac standstill is maintained for at least 2 seconds.

25. The system of claim 22, wherein an electrical current is applied to the vagus nerve using the electrodes, the electrical current being in the range of 10 to 100 Hz (Hertz).

26. The system of claim 22, wherein pulses of electrical current are applied to the vagus nerve using the electrode for less than about 30 seconds.

27. The system of claim 22, wherein the electrical stimulation is initiated automatically when a specified cardiac event is detected.

28. The system of claim 22, wherein the controller is configured to convert ventricular tachycardia or ventricular fibrillation to normal cardiac rhythm.

* * * * *